US008759070B2

(12) United States Patent
Papoutsakis et al.

(10) Patent No.: US 8,759,070 B2
(45) Date of Patent: Jun. 24, 2014

(54) RECOMBINANT CLOSTRIDIA THAT FIX $CO_2$ AND CO AND USES THEREOF

(75) Inventors: Eleftherios T. Papoutsakis, Newark, DE (US); Mohab Ali Al-Hinai, Newark, DE (US); Shawn William Jones, Newark, DE (US); Dinesh Chanukya Indurthi, Newark, DE (US); Daniel Knox Mitchell, Newark, DE (US); Alan Fast, Newark, DE (US)

(73) Assignee: University of Delaware, Newark, DE (US)

( * ) Notice: Subject to any disclaimer, the term of this patent is extended or adjusted under 35 U.S.C. 154(b) by 178 days.

(21) Appl. No.: 13/229,033

(22) Filed: Sep. 9, 2011

(65) Prior Publication Data

US 2012/0064587 A1   Mar. 15, 2012

Related U.S. Application Data

(60) Provisional application No. 61/381,701, filed on Sep. 10, 2010.

(51) Int. Cl.
*C12N 1/20* (2006.01)
*C12N 9/00* (2006.01)

(52) U.S. Cl.
USPC .................. 435/252.2; 148/160; 148/243

(58) Field of Classification Search
None
See application file for complete search history.

(56) References Cited

U.S. PATENT DOCUMENTS

| | | |
|---|---|---|
| 5,807,722 A | 9/1998 | Gaddy |
| 6,340,581 B1 | 1/2002 | Gaddy |
| 2010/0021978 A1 | 1/2010 | Burk et al. |
| 2010/0047890 A1 | 2/2010 | Tracy et al. |
| 2010/0086982 A1 | 4/2010 | Soucaille |
| 2010/0137655 A1 | 6/2010 | Soucaille |
| 2010/0203604 A1* | 8/2010 | Yukawa et al. ............... 435/157 |

FOREIGN PATENT DOCUMENTS

| | | |
|---|---|---|
| WO | WO 2009/036095 A1 | 3/2009 |
| WO | WO 2009/137778 A2 | 11/2009 |

OTHER PUBLICATIONS

Nair and Papoutsakis, "Expression of Plasmid-Encoded aad in *Clostridium acetobutylicum* M5 Restores Vigorous Butanol Production", Journal of Bacteriology, vol. 176, No. 18, pp. 5843-5846 (Sep. 1994).*
PCT/US2011/051006 International Search Report by Kim Lee Yon dated Apr. 27, 2012.
Altschul et al. (1990). "Basic Local Alignment Search Tool." *Journal of Molecular Biology* 215(3): 403-410.
Amador-Noguez, et al. (2010). "Systems-Level Metabolic Flux Profiling Elucidates a Complete, Bifurcated Tricarboxylic Acid Cycle in *Clostridium acetobutylicum.*" *Journal of Bacteriology* 192(17): 4452-4461.
Axley, et al. (1991). "Catalytic properties of an *Escherichia-coli* formate dehydrogenase mutant in which sulfur replaces selenium." *Proceedings of the National Academy of Sciences of the United States of America* 88(19): 8450-8454.
Bannam, T. L. and J. I. Rood (1993). "*Clostridium perfringens—Escherichia coli* shuttle vectors that carry single antibiotic resistance determinants." *Plasmid* 29(3): 233-235.
Benbassat, et al. (1980). "Distribution of Methanol Carbon between Assimilation and Oxidation Pathways in Methanol-Grown Pseudomonas-C." *Journal of General Microbiology* 116(Jan): 213-223.
Bender and Ragsdale (2011) "Evidence That Ferredoxin Interfaces with an Internal Redox Shuttle in Acetyl-CoA Synthase during Reductive Activation and Catalysis." *Biochemistry* 50(2): 276-286.
Bertram, et al. (1991) "Natural transfer of conjugative transposon Tn916 between gram-positive and gram-negative bacteria." *Journal of Bacteriology* 173(2):443.
Borden, et al. (2010). "A genomic-library based discovery of a novel, possibly synthetic, acid-tolerance mechanism in *Clostridium acetobutylicum* involving non-coding RNAs and ribosomal RNA processing." *Metab Eng* 12(3): 268-281.
Cornillot, et al. (1997). "The genes for butanol and acetone formation in *Clostridium acetobutylicum* ATCC 824 reside on a large plasmid whose loss leads to degeneration of the strain." *J Bacteriol* 179(17): 5442-5447.
Drake, H. L. and S. L. Daniel (2004). "Physiology of the thermophilic acetogen *Moorella thermoacetica.*" *Res Microbiol* 155(10): 869-883.
Ezeji, et al. (2007). "Bioproduction of butanol from biomass: from genes to bioreactors." *Current Opinion in Biotechnology* 18(3): 220-227.
Frostl, et al. (1996). "Effect of nitrate on the autotrophic metabolism of the acetogens *Clostridium thermoautotrophicum* and *Clostridium thermoaceticum.*" *J Bacteriol* 178(15): 4597-4603.
Garnier, T. and S. T. Cole (1988). "Identification and molecular genetic analysis of replication functions of the bacteriocinogenic plasmid pIP404 from *Clostridium perfringens.*" *Plasmid* 19(2): 151-160.
Gheshlaghi, et al. (2009). "Metabolic pathways of clostridia for producing butanol." *Biotechnol Adv.* 27(6): 764-781.
Harris, et al. (2001). "Fermentation characterization and flux analysis of recombinant strains of *Clostridium acetobutylicum* with an inactivated solR gene." *Journal of Industrial Microbiology & Biotechnology* 27(5): 322-328.
Harris, et al. (2000). "Characterization of recombinant strains of the *Clostridium acetobutylicum* butyrate kinase inactivation mutant: Need for new phenomenological models for solventogenesis and butanol inhibition?" *Biotechnology and Bioengineering* 67(1): 1-11.
Hartman, et al. (2011). "Construction and characterization of a lactose-inducible promoter system for controlled gene expression in *Clostridium perfringens.*" *Applied and Environmental Microbiology* 77(2): 471-478.

(Continued)

*Primary Examiner* — Anand Desai
(74) *Attorney, Agent, or Firm* — RatnerPrestia

(57) ABSTRACT

The present invention relates a recombinant *Clostridium* expressing one or more heterologous Wood-Ljungdahl (WL) genes. In particular, the recombinant *Clostridium* produces a metabolite at an increased level. The present invention also relates to a method for producing a metabolite by the recombinant *Clostridium*.

19 Claims, 14 Drawing Sheets

(56) References Cited

OTHER PUBLICATIONS

Heap, et al. (2009). "A modular system for *Clostridium* shuttle plasmids." *J Microbiol Methods* 78(1): 79-85.

Hillmann, et al. (2008). "PerR acts as a switch for oxygen tolerance in the strict anaerobe *Clostridium acetobutylicum*." *Molecular Microbiology* 68(4): 848-860.

Jeon et al. (2001). "Purification and characterization of membrane-associated CooC protein and its functional role in the insertion of nickel into carbon monoxide dehydrogenase from *Rhodospirillum rubrum*." *Journal of Biological Chemistry* 276(42): 38602-38609.

Jones, et al. (2008). "The transcriptional program underlying the physiology of clostridial sporulation." *Genome Biol* 9(7): R114.

Jones, et al. (2011). "Inactivation of sigma(F) in *Clostridium acetobutylicum* ATCC 824 Blocks Sporulation Prior to Asymmetric Division and Abolishes sigma(E) and sigma(G) Protein Expression but Does Not Block Solvent Formation." *Journal of Bacteriology* 193(10): 2429-2440.

Kanehisa and Goto (2000). "KEGG: Kyoto Encyclopedia of Genes and Genomes." *Nucleic Acids Research* 28(1): 27-30.

Khan, S. A. (1997). "Rolling-circle replication of bacterial plasmids." *Microbiol Mol Biol Rev* 61(4): 442-455.

Kopke, et al. (2010). "*Clostridium ljungdahlii* represents a microbial production platform based on syngas." *Proceedings of the National Academy of Sciences of the United States of America* 107(29): 13087-13092.

Lee, et al. (1993). "Determination of plasmid copy number and stability in *Clostridium acetobutylicum* ATCC 824." *FEMS Microbiol Lett* 108(3): 319-323.

Lundie, L. L., Jr. and H. L. Drake (1984). "Development of a minimally defined medium for the acetogen *Clostridium thermoaceticum*." *J Bacteriol* 159(2): 700-703.

McLaughlin, et al. (1985). "Gas chromatography and gateway sensors for on-line state estimation of complex fermentations (butanol-acetone fermentation)." *Biotechnol Bioeng* 27(8): 1246-1257.

Mermelstein, et al. (1992). "Expression of Cloned Homologous Fermentative Genes in *Clostridium-acetobutylicum* Atcc 824." *Bio-Technology* 10(2): 190-195.

Mermelstein, L. D. and E. T. Papoutsakis (1993). "Invivo Methylation in *Escherichia-coli* by the *Bacillus-subtilis* Phage-Phi-3t-I Methyltransferase to Protect Plasmids from Restriction Upon Transformation of *Clostridium-acetobutylicum* Atcc-824." *Applied and Environmental Microbiology* 59(4): 1077-1081.

Miller, T. L. and M. J. Wolin (1974). "A serum bottle modification of the Hungate technique for cultivating obligate anaerobes." *Appl Microbiol* 27(5): 985-987.

Monod, et al. (1986). "Sequence and properties of pIM13, a macrolide-lincosamide-streptogramin B resistance plasmid from *Bacillus subtilis*." *J Bacteriol* 167(1): 138-147.

Monot, et al. (1982). "Acetone and Butanol Production by *Clostridium-acetobutylicum* in a Synthetic Medium." *Applied and Environmental Microbiology* 44(6): 1318-1324.

Nolling, et al. (2001). "Genome sequence and comparative analysis of the solvent-producing bacterium *Clostridium acetobutylicum*." *Journal of Bacteriology* 183(16): 4823-4838.

Papoutsakis, E. T. (2008). "Engineering solventogenic Clostridia." *Current Opinion in Biotechnology*. 19(5): 420-429.

Paredes, et al. (2005). "A comparative genomic view of clostridial sporulation and physiology." *Nature Reviews Microbiology* 3(12): 969-978.

Paul, et al. (2010). "Genome sequence of the solvent-producing bacterium *Clostridium carboxidivorans* strain P7T." *Journal of Bacteriology* 192(20): 5554-5555.

Pierce, et al. (2008). "The complete genome sequence of *Moorella thermoacetica* (f. *Clostridium thermoaceticum*)." *Environmental Microbiology* 10(10): 2550-2573.

Projan, et al. (1987). "Replication properties of pIM13, a naturally occurring plasmid found in *Bacillus subtilis*, and of its close relative pE5, a plasmid native to *Staphylococcus aureus*." *J Bacteriol* 169(11): 5131-5139.

Ragsdale, S. W. (1997). "The eastern and western branches of the Wood/Ljungdahl pathway: how the east and west were won." *Biofactors* 6(1): 3-11.

Ragsdale, S. W. and E. Pierce (2008). "Acetogenesis and the Wood-Ljungdahl pathway of CO2 fixation." *Biochimica Et Biophysica Acta-Proteins and Proteomics* 1784(12): 1873-1898.

Sakai et al. (2004) "Ethanol production from $H_2$ and $CO_2$ by a newly isolated thermophilic bacterium, *Moorella* sp. HUCC22-1." *Biotechnology Letters* 26:1607-1612.

Sakai et al. (2005) "Acetate and Ethanol Production from $H_2$ and $CO_2$ by *Moorella* sp. Using a Repeated Batch Culture." *Journal of Bioscience and Bioengineering* vol. 99, No. 3, 252-258.

Santos, et al. (2011). "Optimization of a heterologous pathway for the production of flavonoids from glucose." *Metabolic Engineering* 13(4): 392-400.

Sass et al. (1993). "Isolation of Mutants of *Clostridium acetobutylicum* ATCC 824 Deficient in Protease Activity." *Current Microbiology* vol. 26, pp. 151-154.

Sebaihia, et al. (2006). "The multidrug-resistant human pathogen *Clostridium difficile* has a highly mobile, mosaic genome." *Nature Genetics* 38(7): 779-786.

Seifritz, et al. (1993). "Nitrate as a preferred electron sink for the acetogen *Clostridium thermoaceticum*." *J Bacteriol* 175(24): 8008-8013.

Sillers, et al. (2008). "Metabolic engineering of the non-sporulating, non-solventogenic *Clostridium acetobutylicum* strain M5 to produce butanol without acetone demonstrate the robustness of the acid-formation pathways and the importance of the electron balance." *Metab Eng* 10(6): 321-332.

Sillers, et al. (2009). "Aldehyde-Alcohol Dehydrogenase and/or Thiolase Overexpression Coupled With CoA Transferase Downregulation Lead to Higher Alcohol Titers and Selectivity in *Clostridium acetobutylicum* Fermentations." *Biotechnology and Bioengineering* 102(1): 38-49.

StimHerndon, et al. (1996). "Analysis of degenerate variants of *Clostridium acetobutylicum* ATCC 824." *Anaerobe* 2(1): 11-18.

Thauer, et al. (1977). "Energy conservation in chemotrophic anaerobic bacteria." *Bacteriol Rev.* 41(1): 100-180.

Tomas, et al. (2003). "DNA array-based transcriptional analysis of asporogenous, nonsolventogenic *Clostridium acetobutylicum* strains SKO1 and M5." *Journal of Bacteriology* 185(15): 4539-4547.

Tracy, et al. (2011). "Inactivation of sigma(E) and sigma(G) in *Clostridium acetobutylicum* Illuminates Their Roles in Clostridial-Cell-Form Biogenesis, Granulose Synthesis, Solventogenesis, and Spore Morphogenesis." *Journal of Bacteriology* 193(6): 1414-1426.

Tummala, et al. (1999). "Development and characterization of a gene expression reporter system for *Clostridium acetobutylicum* ATCC 824." *Appl Environ Microbiol* 65(9): 3793-3799.

Wiesenborn, et al. (1988). "Thiolase from *Clostridium acetobutylicum* ATCC 824 and Its Role in the Synthesis of Acids and Solvents." *Appl Environ Microbiol* 54(11): 2717-2722.

Yamaguchi, Y. and M. Inouye (2009). "mRNA interferases, sequence-specific endoribonucleases from the toxin-antitoxin systems." *Progress in molecular biology and translational science* 85: 467-500.

Young et al. (1999). "6 Genetic Methods in Clostridia." *Methods in Microbiology* vol. 29, pp. 191-207.

Zhang, et al. (2006). "mazF, a novel counter-selectable marker for unmarked chromosomal manipulation in *Bacillus subtilis*." *Nucleic acids research* 34:e71.

Supplementary European Search Report for Application No. EP 11 82 4180 by Jakub Celler dated Feb. 11, 2014.

\* cited by examiner

Figure 4

```
ATG GTA AGC AGG TAC GTA CCT GAT ATG GGA GAT TTA ATA TGG GTT GAT TTT GAT CCT
ACA AAA GGA AGT GAG CAA GCT GGA CAT AGA CCA GCT GTT GTT TTA AGT CCT TTT ATG
TAT AAT AAT AAA ACA GGA ATG TGT TTA TGT GTT CCT TGT ACA ACA CAA TCA AAA GGA
TAT CCT TTT GAA GTT GTT TTA TCA GGA CAA GAA AGA GAT GGA GTA GCA TTA GCT GAT
CAA GTA AAA AGT ATA GCA TGG AGA GCA AGA GGA GCA ACA AAA AAA GGA ACA GTT GCA
CCA GAG GAA TTA CAA TTA ATA AAA GCA AAA ATA AAT GTA TTA ATA GGA TAC
```

RECOMBINANT CLOSTRIDIA THAT FIX CO₂ AND CO AND USES THEREOF

CROSS-REFERENCE TO RELATED APPLICATION

This application claims the benefit of U.S. Provisional Application No. 61/381,701, filed Sep. 10, 2010, the content of which is incorporated herein by reference in its entirety for all purposes.

REFERENCE TO U.S. GOVERNMENT SUPPORT

This work is supported by a grant from the U.S. Advanced Research Projects Agency—Energy (ARPA-E) of Department of Energy (DOE) (Award No. 5710002809). The United States has certain rights in the invention.

FIELD OF THE INVENTION

The invention relates generally to recombinant Clostridia expressing one or more heterologous genes required for a functional Wood-Ljungdahl (WL) pathway, and the uses thereof for producing desirable metabolites.

BACKGROUND OF THE INVENTION

Biological carbon dioxide ($CO_2$) fixation by non-photosynthetic microbes holds a great promise for producing useful products (e.g., chemicals and biofuels) from $CO_2$ (which requires an electron source as well, such as $H_2$). Among the non-photosynthetic carbon fixation pathways, the most important one is the Wood-Ljungdahl (WL) pathway in that it is the only linear pathway known to fix carbon. This is practically significant in that $CO_2$ can serve as the sole carbon source as long as there is an electron source, such as $H_2$. The WL pathway is employed by anaerobic organisms, most of which are of the Clostridia class, and are broadly known as acetogens that they fix $CO_2$ and $H_2$ to produce acetate. These organisms are responsible for the production of about 10% of the 100 billion U.S. tons of acetic acid which is produced annually on earth. Thus, they fix billions of tons of $CO_2$ on the earth every year and produce 10 billions tons of acetate. Clostridia are Gram-positive, strict anaerobic endospore-formers, are mostly soil organisms, and belong to the phylum Firmicutes. The Clostridia class includes many families, genera (including *Clostridium* and *Moorella*), and is made up of hundreds of known species.

The WL pathway is found in over 100 species of anaerobic bacteria, many of which are in the class Clostridia. The best known among them are the acetogenic Clostridia, such as *Clostridium aceticum*, *Clostridium difficile*, *C. ljungdahli* and *Moorella thermoacetica* (formerly *Clostridium thermoaceticum*) and, also, *Acetobacterium woodii*. Besides a strong medical interest in these organisms, Clostridia, with or without a native WL pathway, have been the organisms of choice for the biological production of solvents and butanol. For example, *C. acetobutylicum*, though without a full and functional WL pathway, is a Gram-positive obligate anaerobe that is well-known industrially for its ability to produce commodity chemicals (e.g., butyrate, acetate, acetoin, and acetone) and biofuels (e.g., butanol and ethanol).

There remains a need to engineer Clostridia and other anaerobes without a functional WL pathway to improve their metabolism of $CO_2$ as a carbon source for production of useful chemicals and biofuels.

SUMMARY OF THE INVENTION

The present invention relates to recombinant Clostridia expressing one or more heterologous Wood-Ljungdahl (WL) genes. The recombinant Clostridia produce desirable metabolites at an increased level.

According to one aspect of the present invention, a recombinant *Clostridium* expressing one or more heterologous Wood-Ljungdahl (WL) genes derived from a donor *Clostridium* is provided. The recombinant *Clostridium* is derived from a recipient *Clostridium*. The recipient *Clostridium* does not have a functional WL pathway while the donor *Clostridium* has a functional WL pathway. The recombinant *Clostridium* may have a functional WL pathway. At least one of the one or more heterologous Wood-Ljungdahl pathway genes may be integrated into the genome of the recombinant *Clostridium*.

The recombinant *Clostridium* may produce a metabolite at an increased level compared with the recipient *Clostridium*. The metabolite may be a chemical, biofuel, or biofuel precursor. The chemical may be selected from the group consisting of a carboxylic acid, isopropanol, butanediol, acetoin and propanediol. The carboxylic acid may be butyrate or acetate. The biofuel may be selected from the group consisting of ethanol, n-butanol, i-butanol and 2-butanol.

The recipient *Clostridium* may be employed to produce a metabolite. The recipient *Clostridium* may be a solventogenic *Clostridium*. The solventogenic *Clostridium* may be selected from the group consisting of *C. acetobutylicum*, *C. beijerinckii*, *C. saccharoperbutylacetonicum*, and *C. madisonii*. Preferably, the recipient recombinant *Clostridium* is *C. acetobutylicum*.

The recipient *Clostridium* may be a cellulolytic *Clostridium*. The cellulolytic *Clostridium* may be selected from the group consisting of *C. thermocellum*, *C. phytofermentans*, and *C. cellulolyticum*. The donor *Clostridium* may be selected from the group consisting of *M. thermoacetica*, *C. carboxidivorans*, *C. difficile*, and *C. ljungdahlii*. Preferably, the donor *Clostridium* is *C. difficile* or *C. ljungdahlii*.

According to another aspect of the present invention, a method of producing a metabolite is provided. The method comprises culturing the recombinant *Clostridium* of the present invention in a culture medium, whereby the recombinant *Clostridium* produces the metabolite at an increased level compared with the recipient *Clostridium*. The method further comprise recovering the metabolite from the recombinant *Clostridium* or the culture medium. The metabolite may be selected from the group consisting of acetate, ethanol, butyrate, acetoin and butanol. The *Clostridium* is preferably *C. acetobutylicum*. The donor *Clostridium* is preferably *C. difficile* or *C. ljungdahlii*.

BRIEF DESCRIPTION OF THE DRAWINGS

FIG. 4 shows the optimized mazF DNA sequence (SEQ ID NO: 1) useful for a double crossover integration.

DETAILED DESCRIPTION OF THE INVENTION

The present invention is based on the discovery that expressing heterogonous genes required for the Wood-Ljungdahl (WL) pathway in a *Clostridium* not having a functional WL pathway improves metabolism of $CO_2$ by the *Clostridium*. The present invention relates to engineering a *Clostridium* not having a functional WL pathway by expressing heterologous WL genes in the engineered or recombinant *Clostridium*. The recombinant *Clostridium* produces desirable metabolites at an increased level.

The term "polynucleotide" used herein refers to a polymer of nucleotide residues with no limitation with respect to the minimum length of the polymer. Preferably, the polynucleotide has at least 60 nucleotides. The polynucleotide may be a DNA, cDNA or RNA molecule.

The term "variant" of a polynucleotide as used herein refers to a polynucleotide having a nucleic acid sequence that is the same as the nucleic acid sequence of the polynucleotide except having at least one nucleic acid modified, for example, deleted, inserted, or replaced, respectively. The variant may have a nucleic acid sequence at least about 80%, 90%, 95%, or 99%, preferably at least about 90%, more preferably at least about 95%, identical to the nucleic acid of the polynucleotide.

The term "derived from" used herein refers to the origin or source, and may include naturally occurring and recombinant microorganisms or molecules, or variants thereof. For example, a gene derived from a bacteria may be identical to the corresponding native gene in the bacteria or a variant thereof, i.e., having a nucleic acid sequence at least about 80%, 90%, 95%, or 99%, preferably at least about 90%, more preferably at least about 95%, identical to the corresponding native gene.

The present invention provides a recombinant *Clostridium* expressing one or more heterologous Wood-Ljungdahl (WL) genes derived from a donor *Clostridium*. The recombinant *Clostridium* is derived from a recipient *Clostridium*. While the recipient *Clostridium* does not have a functional WL pathway, the donor *Clostridium* has a functional WL pathway.

Figure 1:
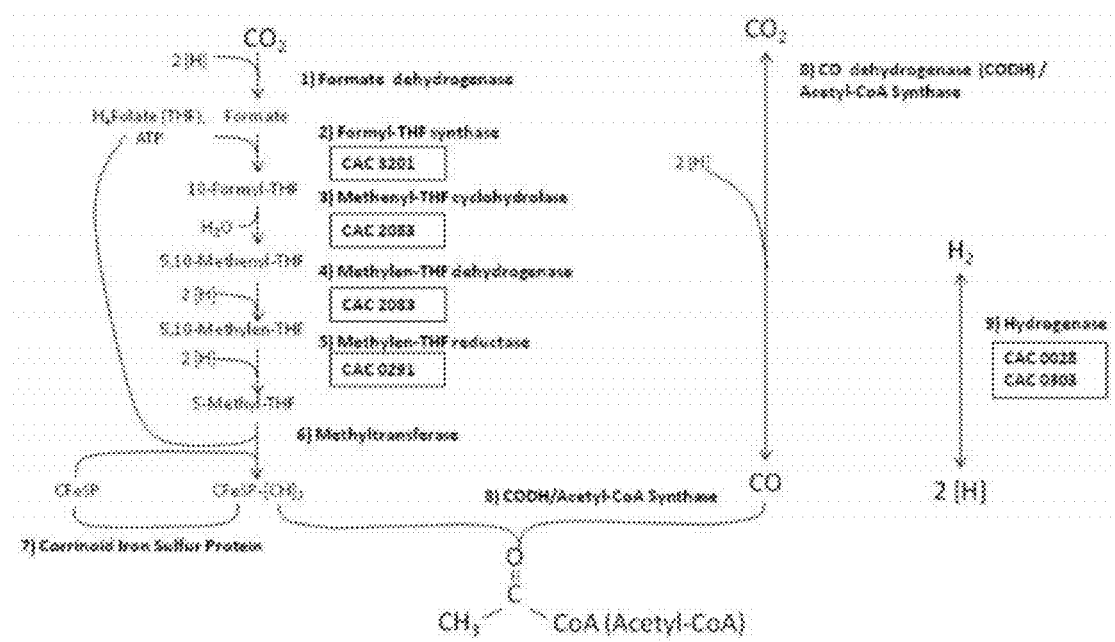
FIG. 1 illustrates the Wood-Ljungdahl pathway with enzyme annotation adapted from Ragsdale et al. (2008) "The complete genome sequence of *Moorella thermoacetica* (f. *Clostridium thermoaceticum*)" *Environmental Microbiology* 10(10): 2550-2573). [H] represents a reducing equivalent. Boxed gene IDs indicate the WL pathway genes natively expressed in *C. acetobutylicum* based on annotation in Kyoto Encyclopedia of Genes and Genomes (KEGG) (Kanehisa and Goto (2000). "KEGG: Kyoto Encyclopedia of Genes and Genomes." *Nucleic Acids Research* 28(1): 27-30).

The Wood-Ljungdahl (WL) pathway has two branches: the Eastern or methyl branch, and the Western or carbonyl branch (FIG. 1). Numerous genes encoding various enzymes are required in each branch to constitute a functional WL pathway. A WL pathway is functional in a bacterium if it enables the bacterium to assimilate carbon in $CO_2$ and/or CO molecules into cellular carbon.

The recombinant *Clostridium* may produce a metabolite at an increased level compared with the recipient *Clostridium*. The metabolite may be a chemical, biofuel, or biofuel precursor. The chemical may be selected from the group consisting of a carboxylic acid, isopropanol, butanediol, acetoin and propanediol. The carboxylic acid may be butyrate or acetate. The biofuel is selected from the group consisting of ethanol, n-butanol, i-butanol and 2-butanol. Preferably, the recombinant *Clostridium* produces acetate, ethanol, butyrate, acetone and/or butanol.

A recipient *Clostridium* is a *Clostridium* that does not have a functional WL pathway, and into which one or more heterogonous WL genes are introduced. Preferably, recipient *Clostridium* is employed to produce a metabolite. For example, it may be a solventogenic *Clostridium* or a cellulolytic *Clostridium*. The solventogenic *Clostridium* may be selected from the group consisting of *C. acetobutylicum*, *C. beijerinckii*, *C. saccharoperbutylacetonicum*, and *C. madisonii*. The cellulolytic *Clostridium* may be selected from the group consisting of *C. thermocellum*, *C. phytofermentans*, and *C. cellulolyticum*. More preferably, the recipient recombinant *Clostridium* is *C. acetobutylicum* (e.g., ATCC 824).

A donor *Clostridium* is a *Clostridium* that has a functional WL pathway, and from which one or more WL genes are obtained. Donor *Clostridium* may be selected from the group consisting of *M. thermoacetica*, *C. carboxidivorans*, *C. difficile*, and *C. ljungdahlii*. Preferably, the donor *Clostridium* is *C. difficile* or *C. ljungdahlii*. More preferably, the donor *Clostridium* is *C. ljungdahlii*.

Figure 2:
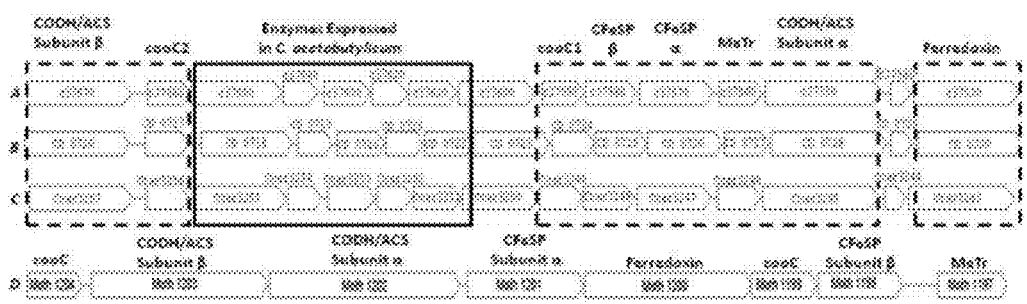
FIG. 2 shows the WL region in the *C. ljungdahlii* (A), *C. difficile* (B), *C. carboxidivorans* (C), and *M. thermoacetica* (D) genomes. The region in the *Clostridium* acetogens is highly conserved in both order and homology. The genes involved in the CO dehydrogenase/acetyl-CoA synthase are also consolidated into one region of *M. thermoacetica* that has different organization than the other examined clostridia; however, the other *M. thermoacetica* WL genes are distributed throughout its chromosome. The dashed boxes contain the enzymes important to pathway functionality that are not present in CAC. The solid box indicate genes already present in *C. acetobutylicum*. The following genes are labeled with their gene product in the: CODH/ACS Subunits (α and β), which comprise the major parts of the CO dehydrogenase/CoA synthase; cooC1 and cooC2, nickel insertion proteins that are required to form the CODH/ACS active sites (Ludden et al. (2001). "Purification and characterization of membrane-associated CooC protein and its functional role in the insertion of nickel into carbon monoxide dehydrogenase from *Rhodospirillum rubrum*." *Journal of Biological Chemistry* 276(42): 38602-38609); CFeSP Subunits (α and β), which form the corrinoid iron/sulfur protein; MeTr, a methyltransferase that carries the methyl- group from 5-methyltetrahydrofolate to the CFeSP; and Ferredoxin, which may be important in regenerating the metal catalytic sites of the CODH/ACS (Ragsdale and Bender (2011) "Evidence That Ferredoxin Interfaces with an Internal Redox Shuttle in Acetyl-CoA Synthase during Reductive Activation and Catalysis." *Biochemistry* 50(2): 276-286).

A "Wood-Ljungdahl (WL) gene" as used herein refers to a full length gene required for a functional WL pathway in a bacterium, or a functional fragment or variant thereof. Some donor Clostridia (e.g., *M. thermoacetica*, *C. carboxidivorans*, *C. difficile*, and *C. ljungdahlii* (CLJ)) have been sequenced. A comparative analysis of their genomes may be used to identify the genes required for a functional WL pathway (i.e., WL genes). For example, a comparative genome analysis was performed using the Basic Local Alignment Search Tool (BLAST) to confirm the correct annotations for each of the WL enzymes as well as which gene products form protein complexes with each other. (Altschul et al. (1990). "Basic Local Alignment Search Tool." *Journal of Molecular Biology* 215(3): 403-410). The BLAST comparison among the WL genes of *C. ljungdahlii*, *C. difficile*, and *C. carboxidivorans* has shown highly conserved regions of the genome (FIG. 2) containing the WL genes that catalyze reactions 2 through 8 listed on the diagram in FIG. 1. The amino acid residues across the three organisms were between 62% and 92% identical for the genes in this region. Further comparison of these three genomes to that of *M. thermoacetica* revealed which gene products form multiprotein complexes. For instance, the genes encoding CODH/ACS subunit α, CODH/ACS subunit β, CFeSP subunit α, and CFeSP subunit β are annotated generically as subunits of the CODH/ACS in the genomes of *C. ljungdahlii*, *C. difficile*, and *C. carboxidivorans*. Given the α- and β-subunits of these proteins, the expression vectors may be designed with both subunits on the same vector and under the same promoter; therefore, variability in promoter strength and plasmid copy number may not alter the relative mRNA levels for each subunit. In addition to the common genes found in the WL region, a formate dehydrogenase (FDH), which catalyzes the first reaction in the Eastern branch, was found in *C. ljungdahlii*, *C. difficile*, and *C. carboxidivorans*.

A recipient *Clostridium* may lack one or more genes required for a functional WL pathway (i.e., WL genes). A genome comparative analysis of a recipient *Clostridium* and a donor *Clostridium* may be used to identify the missing WL genes. For example, *C. acetobutylicum* does not have a functional WL pathway but does have a number of homologs to components of the WL pathway (Table 1).

TABLE 1

Homologs of the WL pathway in *M. thermoacetica*, *C. difficile* and *C. acetobutylicum*

| | | Genes of Wood Ljungdahl pathway in: | | | Protein identity between: | |
|---|---|---|---|---|---|---|
| | *M. thermoacetica* (MTA) | *C. acetobutylicum* (CAC) | *C. difficile* (CDF) | MTA/CAC | MTA/CDF | CDF/CAC |
| Eastern | Moth_2312 | — | CD3317 | — | 32.7% | — |
| | Moth_2314 | CAC0764 | CD1537 | 21.5% | 26.6% | 37.1% |
| | Moth_0109 | CAC3201 | CD0718 | 64.8% | 66.2% | 62.1% |
| | Moth_1516 | CAC2083 | CD0720 | 44.1% | 42.1% | 37.1% |
| | Moth_1191 | CAC0291 | CD0722 | 12.5% | 38.6% | 13.1% |
| Western | Moth_1197 | CAC0578 | CD0727 | 6.3% | 37.6% | 6.8% |
| | Moth_1201 | — | CD0726 | — | 37.8% | — |
| | Moth_1198 | — | CD0725 | — | 38.0% | — |
| | Moth_1203 | CAC2498/0116 | CD0716 | 29.8%/27.5% | 38.5% | 30.2%/29.8% |
| | Moth_1202 | — | CD0728 | — | 46.1% | — |

The first homolog in *C. acetobutylicum* is the β-subunit of the formate dehydrogenase, which reduces $CO_2$ to formate in the first reaction in the Eastern branch of the WL pathway. In *M. thermoacetica*, this enzyme is made up of α and β subunits, Moth_2312 and Moth_2314, respectively. However a potential homolog has been only found for the β-subunit in *C. acetobutylicum*. For the remaining enzymes in the Eastern branch, good homologs have been found except for one. CAC0291 has poor homology but is a bifunctional enzyme in *C. acetobutylicum*, which codes for both the needed methylenetetrahydrofolate reductase and a homocysteine S-methyltransferase.

Unlike the Eastern branch, *C. acetobutylicum* is missing most of the enzymes from the Western branch. The only good homologs which have been found in *C. acetobutylicum* are two carbon monoxide dehydrogenases. A second potential homolog is a methyltetrahydrofolate methyltransferase, CAC0578, which has very poor protein identity with the corresponding enzyme in both *M. thermoacetica* and *C. difficile*. However, CAC0578 is annotated as being able to catalyze the reaction from methyl-$H_4$folate to $H_4$folate, the reaction that the *M. thermoacetica* and *C. difficile* enzymes carry out. The remaining components of the Wood-Ljungdahl pathway, the corrinoid iron-sulfate protein (CFeSP) and the acetyl-CoA synthase, have no homologs in *C. acetobutylicum*.

All these homologs identified in *C. acetobutylicum* (and all genes belonging in the same operon with those) are highly expressed. Expression of these genes may not restrict the ability to institute a functional WL pathway in *C. acetobutylicum*.

Once the missing WL genes are identified in a recipient *Clostridium*, some or all of these WL genes may be introduced into and expressed in the recipient *Clostridium* to generate a recombinant *Clostridium* using techniques known in the art. Preferably, the recombinant *Clostridium* contains a full set of WL genes, and has a functional WL pathway. For example, WL genes, including: a formate dehydrogenase (CD3317, 2.1 kb), the CFeSP α-subunit (CD0726, 1.4 kb), the CFeSP β-subunit (CD0725, 0.9 kb), an acetyl-CoA synthase (CD0728, 2.1 kb), a methyltetrahydrofolate methyltransferase (CD0727, 0.8 kb), and the β-subunit of the formate dehydrogenase (CD1537, 1.4 kb), may be introduced into *C. acetobutyllcum* to generate a functional WL pathway in the *C. acetobutyllcum*. These WL genes may be derived from *C. difficile*, which has a functional WL pathway and is a closer relative to *C. acetobutylicum* than *M. thermoacetica*. Genomic *C. difficile* DNA may be purchased from ATCC to amplify all these WL genes using PCR. To enable and/or enhance $CO_2$ fixation by *C. acetobutylicum*, additional WL genes such as CD0727 from *C. difficile*, the β-subunit of the formate dehydrogenase from *C. difficile*, and/or WL genes from *M. thermoacetica* genomic DNA may also be introduced into *C. acetobutylicum*.

In the recombinant *Clostridium*, a heterologous WL gene may be maintained in a self-replicating plasmid or integrated into the genome of the recombinant *Clostridium*. When the recombinant *Clostridium* comprises two or more heterogonous WL genes, some or all of the heterogonous WL genes may be integrated into the genome of the recombinant *Clostridium*, or carried in two or more co-existing plasmids, which preferably have compatible replication origins.

Two plasmids may be used to express these genes in *C. acetobutylicum*. In order to stably maintain two plasmids within a cell, the plasmids' replication origins (origins of replication/ORI/replicon) must be compatible to ensure that the cell's replication machinery is not diluted, or become biased, replicating one plasmid or the other. For example, the Gram-positive origin of replication (repL), from the *B. subtilis* cryptic plasmid pIM13, is compatible with the *Clostridium perfringens* pIP404 ORI found in the pJIR750 shuttle vector (American Type Culture Collection, Manassas, Va.) in *C. acetobutylicum*. Wild-type *C. acetobutylicum* was transformed with plasmid pJIR750 as previously described (Mermelstein and Papoutsakis (1993). "In vivo Methylation in *Escherichia-Coli* by the *Bacillus-Subtilis* Phage-Phi-3t-I Methyltransferase to Protect Plasmids from Restriction Upon Transformation of *Clostridium-Acetobutylicum* Atcc-824." *Applied and Environmental Microbiology* 59(4): 1077-1081). Transformants were plated onto 2×YTG plates supplemented with 5 μg/ml thiamphenicol. Following 36 hours of incubation, the plates were stored at room temperature for 7 days to allow for spore development. Resistant colonies were selected, heat shocked at 80° C. for 10 minutes and grown in 10 ml CGM supplemented with the appropriate antibiotic. The plasmid was then purified and transformed into *E. coli* TOP10 (Invitrogen) cells. Two hundred microliters of the transformants were plated onto LB plates supplemented with 35 μg/ml chloramphenicol. Resistance colonies were selected, and the plasmids mini-prepped and confirmed by restriction digests. The repL bearing plasmid, pSOS94del, was subsequently transformed into 824(pJIR750). Transformants were plated onto 2×YTG plates supplemented with 5 μg/ml thiamphenicol and 40 μg/ml erythromycin. After 36 hours of incubation, the plates were stored at room temperature for 7 days to allow for spore development. Resistant colonies were selected, heat shocked at 80° C. for 10 minutes and grown in 10 ml CGM supplemented with the appropriate antibiotics. The plasmids were then purified and transformed into *E. coli* TOP10 (Invitrogen) cells. Two hundred microliters of the transformants were plated onto LB plates supplemented with 35 μg/ml chloramphenicol and another 200 μl were plated onto LB plates supplemented with 50 μg/ml ampicillin. Resistance colonies from each plate were selected, and the plasmids mini-prepped and confirmed by restriction digests. This strategy may be extended to identifying and testing additional plasmids (3 or more) that co-exist if a large number of genes needs to be expressed. The biological principles of co-existing plasmids apply whether the plasmids are 2, 3 or more.

Figure 3:
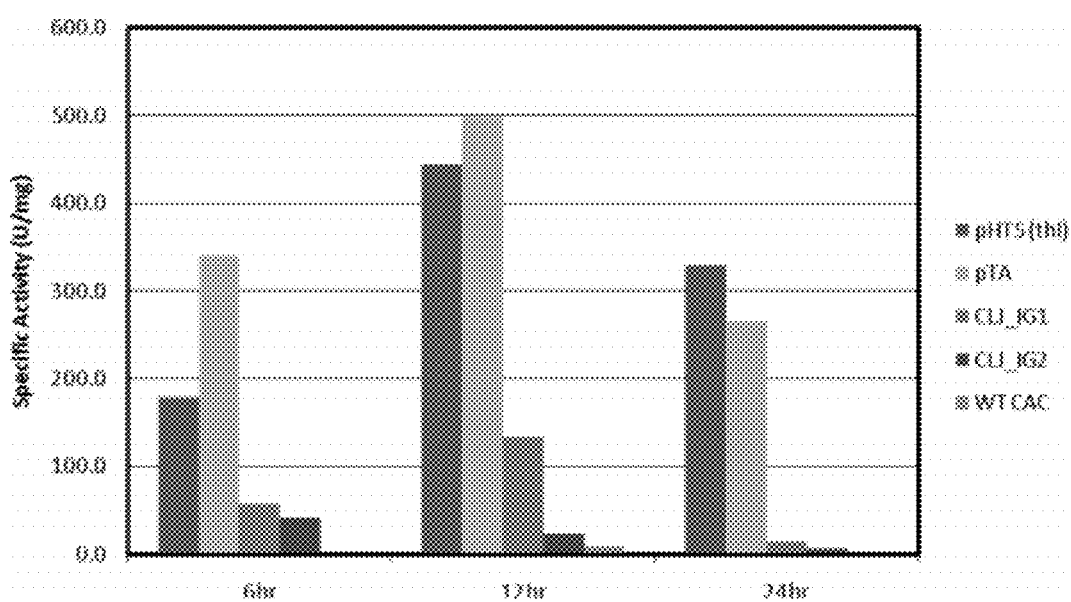
FIG. 3 shows promoter activity as determined by the β-galactosidase assay with samples taken at 6 hr, 12 hr, and 24 hr timepoints.

A number of different promoters may be used to overexpress the WL genes in the recombinant strain of *C. acetobutylicum*. These include the previously described thiolase promoter ($p_{thl}$) and the phosphotransbutyrylase promoter ($p_{ptb}$), both derived from *C. acetobutylicum*, the newly characterized phosphotransacetylase promoter ($p_{pta}$), derived from upstream region of the phosphotransacetylase gene (pta) in *C. acetobutylicum* (FIG. 3), and also two promoters ($p_{IG1}$ and $p_{IG2}$) from *C. ljungdahlii* that give expression in *C. acetobutylicum*. As shown in FIG. 3, the $p_{thl}$ and $p_{pta}$ are both highly expressed at all of the sample timepoints. The promoters from CLJ IG1 and IG2 both showed low, but measurable, levels of expression. If needed, additional promoters may be created by isolating the upstream regions of genes with known levels of expression. The promoters that provide the highest expression in *C. acetobutylicum* are $p_{thl}$, $p_{pta}$, and $p_{ptb}$, which are highly expressed throughout exponential growth, whereas the heterologous promoters derived from the WL region in *C. ljungdahlii* provide a lower level of expression in *C. acetobutylicum*. Having promoters with both high and low expression levels allows one to tailor expression and correct imbalanced gene ratios, which has previously been shown as an important tool for improving pathway expression and production.

In order to expand the genome of *C. acetobutylicum* with genes encoding the WL pathway from *C. ljundahlii*, a single crossover integration method may be employed using a suicide plasmid. Briefly, a suicide plasmid (i.e., with no origin of replication that is functional in *C. acetobutylicum*) containing the *B. subtilis* resolvase gene recU (to enhance recombination efficiency in *C. acetubutylicum*) nay be constructed. In addition to the recU, the plasmid may contain a sigma factor F (sigF; this is the gene to be disrupted in order to integrate the desirable genes) region of homology, a thiamphenicol resistance marker and a gram negative origin of replication. Clostridial transformation may be performed using techniques know in the art. After transformation, colonies resistant to thimaphenicol may be screened for the integration of the plasmid carrying the heterogeneous WL genes from *C. ljundahlii*. Instead of sigF several other *C. acetobutylicum* genes may be used as a site of integration. Such genes may be chosen from a list of non metabolic genes that would not affect the ability of cells to grow well. The sigF only affects the sporulation process and cells with a disrupted sigF gene grow well.

Figure 5:
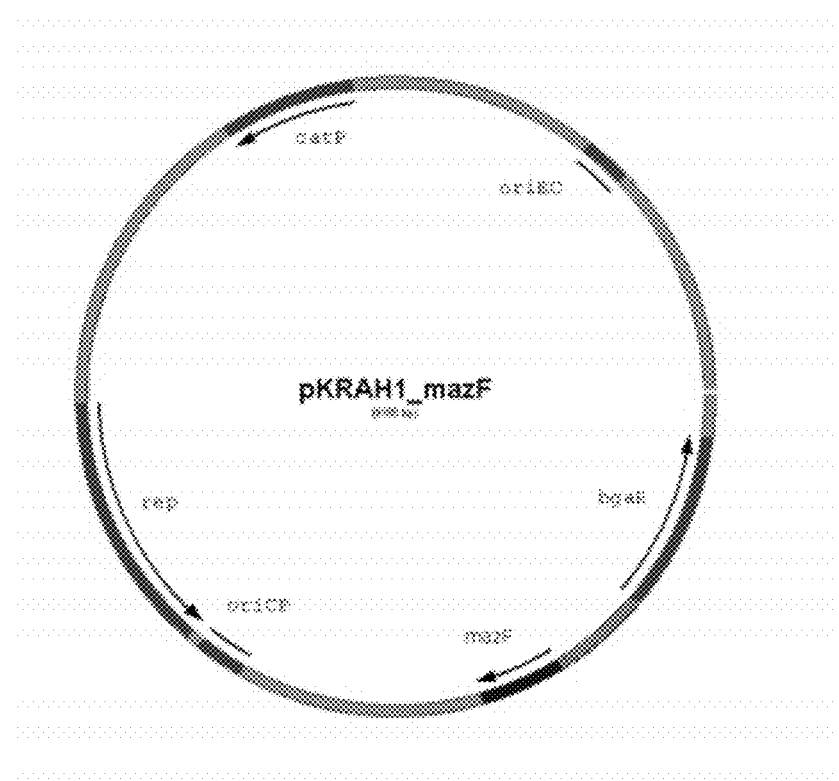
FIG. 5 shows the map of plasmid pKRAH1_mazF. catP, chloramphenicol resistance; oriEC, gram negative origin of replication; bgaR, beta-galactosidase regulator; rep, gram positive replication protein; oriCP, gram positive origin or replication; mazF, MazF transcript.
Figure 6:
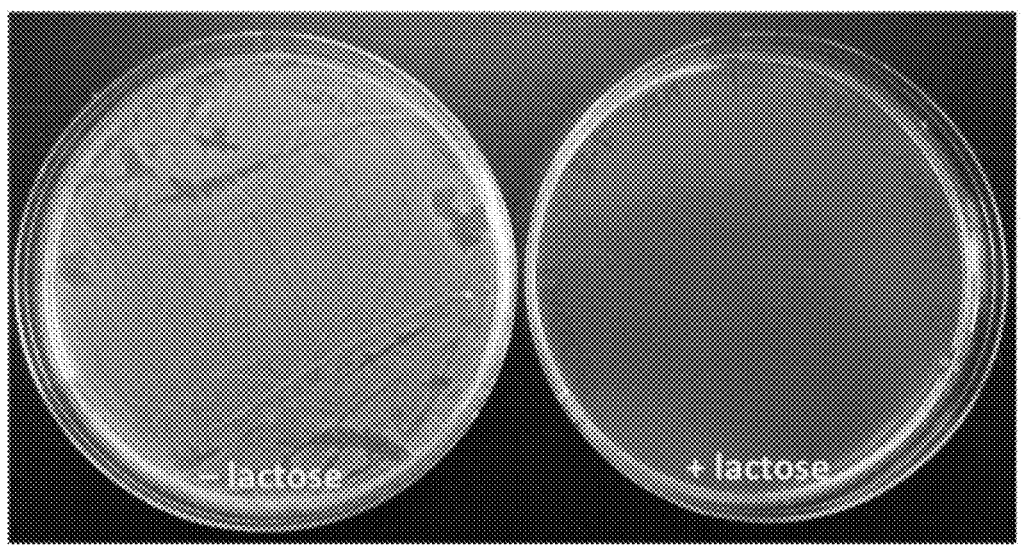
FIG. 6 shows cell survival upon induced expression of mazF. On media lacking lactose, the mazF transcript was not transcribed; therefore cells grew and survived normally. On media containing 40 mM lactose, cells transcribed and translated the optimized mazF gene which was lethal to the cells and hence no colonies were seen on the plate.
Figure 7:
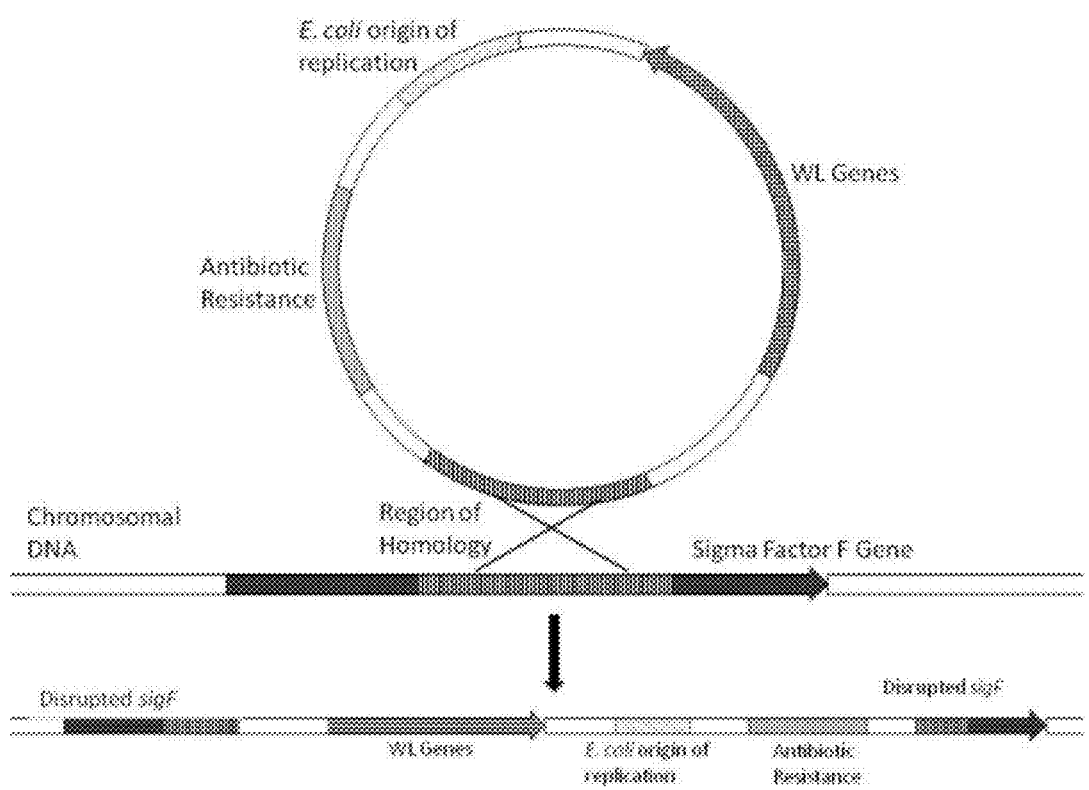
FIG. 7 illustrates a chromosomal integration with a non-replicating vector, a chromosomal target of integration, and an integration product.

A double crossover integration method may also be adopted by utilizing a novel counter-selection marker MazF under the control of a lactose inducible promoter. The counter-selection marker was developed utilizing a codon optimized mazF gene for optimal expression in *C. acetobutylicum*. The MazF, a mRNA interferase, has been successfully used as a counter-selection marker in *C. acetobutylcum* ATCC824. The MazE-MazF complex is a part of the toxin-antitoxin system present in *E. coli*. The toxin, MazF, is stable while the anti-toxin, MazE, is labile. It was previously reported that MazF was used successfully as a counter-selection marker in *B. subtilis*. The mazF transcript was synthetically constructed (DNA 2.0) for optimized translation in *C. acetobutylicum* ATCC 824 (FIG. 4). A lactose-inducible promoter (bgaR) that was adapted from *C. perfringens* strain 13 was employed in order to exploit the lethality of MazF. Subsequently, it was cloned downstream of the lactose-inducible promoter (bgaR) in plasmid pKRAH1. The newly constructed plasmid containing the lactose-inducible promoter and the codon optimized mazF gene was renamed (pKRAH1_mazF) (FIG. 5). Once expressed and translated, MazF cleaves mRNA at ACA sequences therefore arresting cell growth. The plasmid was electrotransformed in *C. acetobutylicum* ATCC 824. Once the strain bearing the plasmid was confirmed, colonies were grown in liquid media supplemented with the appropriate antibiotic for 24 hours. Subsequently, equal volumes of cell culture were plated to solid 2×YTG media supplemented with the appropriate antibiotic with and without lactose. After 24 hours of incubation at 37° C. in an anaerobic chamber, the plates were visually inspected for cell growth. Plates containing lactose did not have any colonies while those lacking lactose showed an abundance of cells (FIG. 6). The toxicity of MazF enables screening for cells that have undergone double crossover events while losing the plasmid backbone.

Following a genome and functionality analysis, a complete set of WL genes may be introduced into *C. acetobutylicum*. The combined size of this set of WL genes required to confer a functional pathway may be ~15 kb. Three plasmids, each containing a portion of the WL genes, may be constructed: two of them to be integrated into the *C. acetobutylicum* chromosome and one to be maintained as a replicating plasmid in *C. acetobutylicum*. The *C. acetobutylicum* mutant M5 is a degenerated strain of *C. acetobutylicum*, which has lost the pSOL1 megaplasmid, the ability to sporulate, and the ability to produce butanol and acetone, and may be used for cloning the WL genes because transformation efficiency is higher in M5 than in the *C. acetobutylicum* type-strain, ATCC 824.

The first chromosomal integration may be performed with a non-replicating vector—that is, a plasmid without a clostridial origin of replication—consisting of a portion of the WL genes under the control of a strong promoter, a homologous sequence targeting the chromosome, an antibiotic selection marker, and a minimal vector backbone. Because the plasmid is unable to propagate in *C. acetobutylicum*, the only clones that express an antibiotic resistance selection marker would be those in which the vector has integrated. The region of homology on the first integrating vector may target the sigma factor F gene (FIG. 7), a sporulation-related sigma factor that is superfluous in the non-sporulating M5.

The second non-replicating plasmid may also be integrated on the M5 chromosome whereby its region of homology may target and disrupt the selection marker from the first plasmid, allowing the maintenance of two single-crossover integrations with only one antibiotic resistance marker. The vector backbone of the second plasmid may be different from the first, ensuring that the only homologous region is the antibiotic resistance gene. The third plasmid may be maintained as a replicating plasmid. After the cloning steps are completed, the recombinant strain may be cultured under $CO_2$ and $H_2$ to determine to what extent the pathway is functional.

A recombinant *Clostridium* may be maintained or grown in a culture medium. For example, an engineered strain may be grown in serum bottles using a modified Hungate technique (Miller and Wolin (1974). "A serum bottle modification of the Hungate technique for cultivating obligate anaerobes." *Appl Microbiol* 27(5): 985-987) in defined media (Monot et al. (1982). "Acetone and Butanol Production by *Clostridium-Acetobutylicum* in a Synthetic Medium." *Applied and Environmental Microbiology* 44(6): 1318-1324) under $CO_2/H_2$. Briefly, small test tubes may be filled with nonsterile, defined media, and gassed using $CO_2$. After gassing, a butyl rubber stopper may be used to seal the tube and a crimped metal seal may be added. The tube and media may then be autoclaved. Before inoculation, the tubes may be filled with $H_2$ and $CO_2$ (80:20, v/v) to a final pressure of 0.2 MPa. Optimal conditions for *C. acetobutylicum* may be determined empirically using the established art in this field. A defined clostridial medium (Monot et al. (1982). "Acetone and Butanol Production by *Clostridium-Acetobutylicum* in a Synthetic Medium." *Applied and Environmental Microbiology* 44(6): 1318-1324) is used with minimal glucose (1 to 80 g/L can be used). To inoculate and sample the culture, a hypodermic syringe and needle may be used.

The expression of mRNA from cloned WL genes in *C. acetobutylicum* may be determined. For example, semi quantitative RT-PCR may be performed on mid-exponential (6 hr), early stationary (12 hr) and stationary (24 hr) phase cultures of the *C. acetobutylicum* containing heterologously expressed WL genes.

Reverse transcription of total RNA may be carried out with random hexamer primers, using High Capacity cDNA ReverseTranscription Kit (Applied Biosystems). PCR may be performed on 50 ng of cDNA using primers specific to the WL genes. To test for DNA contamination during RNA isolation, equal amount of RNA may be used as a template for PCR using suitable primer sets.

CO-dehydrogenase/Acetyl-CoA synthase protein complex (CLJ_c37670/CLJ_c37550) and corrinoid iron-sulfate protein (CLJ_c37580, CLJ_c37570) form a multi subunit protein complex to be a functional enzyme unit. Therefore, determining mRNA levels of the heterologously expressed genes in *C. acetobutylicum* and comparing them to mRNA levels in an acetogen that natively expresses WL-pathway genes (*C. ljungdahlii*), may be instrumental in understanding transcript levels required to incorporate functional WL-pathway enzymes in *C. acetobutylicum.*

Q-RT PCR may be performed on both *C. acetobutylicum* strains that express WL-pathway genes and wild type *C. ljungdahlii* grown on $CO_2+H_2$. Both *C. acetobutylicum* and *C. ljungdahlii* cultures may be harvested at an $A_{600}$~1.00. RNA isolation followed by Q-RT-PCR may be performed on the samples.

Once the heterogonous WL genes are expressed in *C. acetobutylicum*, expression of proteins/enzymes from the cloned plasmids may be assessed. To determine functionality of the WL proteins in CAC, enzyme assays are conducted on individual strains containing specific enzymes. For example, formate dehydrogenase (FDH) enzyme assay has been performed on *C. acetobutylicum* strain expressing FDH enzyme. Specific activity of the formate dehydrogenase in CAC strain expressing FDH was observed to be 0.331 $mMmin^{-1}mg^{-1}$ (U/mg), in comparison to 0.00 U/mg that was observed in non-recombinant WT-CAC (as it does not have an FDH gene). As a positive control, similar assay has also be performed on wild type *C. ljungdahlii* grown on $CO_2+H_2$, which has functionally active WL-pathway enzymes, and FDH activity of 1.474 U/mg was observed. This demonstrates our proof of concept that functional WL-pathway enzymes can be expressed into CAC from other related bacteria.

Cell pellet was re-suspended under anoxic conditions, in appropriate volume of Z buffer for an $A_{600}$~10-20 in minimum of 500 μl. Components of Z buffer include as detailed previously along with 10 mM dithiothreitol (DTT) and 0.1 mM phenylmethylsulfonyl (PMSF). Cell lysate was prepared under anoxic conditions by vortexing the re-suspended cells in 40 mg of glass beads for 1 min and then incubate on ice for 1 min, for a total of 5 repetitions. Cell debris was removed by centrifugation at 16,000×g for 30 min at 4° C.

Formate dehydrogenase (FDH) activity was determined by performing enzyme activity assay under anoxic conditions. The assay was performed in 50 mM Tris HCl (Ph 8.5) plus 5 mM benzyl viologen as electron acceptor and 20 mM sodium formate as substrate. Reaction was be initiated by adding 10 μl of the cell extract and increase in $A_{578}$ was recorded to determine enzyme activity. Reaction conditions without addition of the substrates may be used as negative controls for the experiment.

Similar enzyme assay experiments may be conducted on other WL proteins like Carbon monoxide dehydrogenase/acetyl-CoA synthase (CODH/ACS). The assay may be performed as mentioned above by using 1 atm of 100% CO as a substrate instead of sodium formate.

In order to test for $CO_2$ uptake and utilization in *C. acetobutylicum*, two assays may be used. The first assay measures simply if there is growth of the organism in the tubes with only $CO_2$ and $H_2$ present, but no other carbon or electron source. In the second assay, the concentration of $CO_2$ and $H_2$ in the headspace of the flask throughout the fermentation is measured via gas chromatography. The recombinant strains consume the $CO_2$ and $H_2$ while the wild-type control shows minimal to no consumption.

To further enhance $CO_2$ and $H_2$ utilization, native *C. acetobutylicum* genes (Table 1) as well the native hydrogen-uptake genes (namely: CAC0028—hydA, CAC0808-0811—hybG-hypE-hypF-hypD, CAC3230—ferredoxin, CAP0141-0143—mbhS-mbhL-hyaD) may be overexpressed using stronger promoters, like the ptb, thl, and the pta (phosphotransacetylase) promoters. Random chemical mutagenesis and transposon mutagenesis may also be used to screen for a strain that uses $CO_2$ and $H_2$ at high rates. After a set of WL genes proves successful in enabling $CO_2$ and $H_2$ utilization and at high rates in a recipient *Clostridium*, these genes may be integrated into the chromosome.

The present invention also provides a method of producing a metabolite. The method comprises culturing the recombinant *Clostridium* of the present invention in a culture medium under conditions permitting that the recombinant *Clostridium* produces the metabolite at an increased level compared with the recipient *Clostridium*. The method further provides recovering the metabolite from the recombinant *Clostridium* or the culture medium.

In a method according to the present invention, the metabolite may be a chemical, biofuel, or biofuel precursor. The chemical may be selected from the group consisting of a carboxylic acid, isopropanol, butanediol, acetoin and propanediol. The carboxylic acid may be butyrate or acetate. The biofuel is selected from the group consisting of ethanol, n-butanol, i-butanol and 2-butanol. Preferably, the recombinant *Clostridium* produces acetate, ethanol, butyrate, acetone and/or butanol.

In a method according to the present invention, the recipient *Clostridium* may be employed to produce a metabolite. For example, it may be a solventogenic *Clostridium* or a cellulolytic *Clostridium*. The solventogenic *Clostridium* may be selected from the group consisting of *C. acetobutylicum, C. beijerinckii, C. saccharoperbutylacetonicum,* and *C. madisonii*. The cellulolytic *Clostridium* may be selected from the group consisting of *C. thermocellum, C. phytofermentans,* and *C. cellulolyticum*. More preferably, the recipient recombinant *Clostridium* is *C. acetobutylicum* (e.g., ATCC 824).

In a method according to the present invention, the donor *Clostridium* may be selected from the group consisting of *M. thermoacetica, C. carboxidivorans, C. difficile,* and *C. ljungdahlii*. Preferably, the donor *Clostridium* is *C. difficile* or *C. ljungdahlii*. More preferably, the donor *Clostridium* is *C. ljungdahlii*.

The term "about" as used herein when referring to a measurable value such as an amount, a percentage, and the like, is meant to encompass variations of ±20% or ±10%, more preferably ±5%, even more preferably ±1%, and still more preferably ±0.1% from the specified value, as such variations are appropriate.

EXAMPLE 1

Construction of p94CD0725-27

Figure 8:
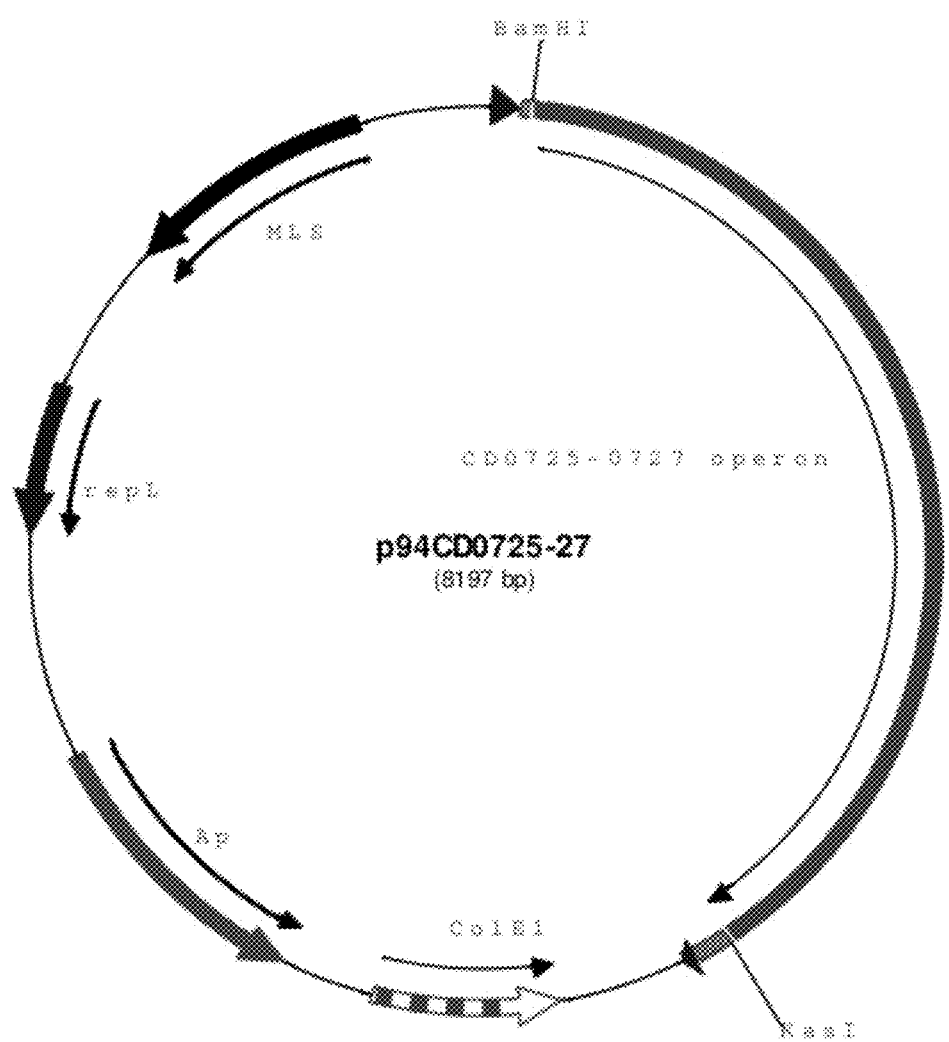
FIG. 8 shows the map of p94CD0725-27 plasmid. MLS region codes for erythromycin resistance and Ap region codes for amplicillin resistance.

Three genes necessary for the Western branch of the WL pathway: CFeSP α-subunit (CD0726), CFeSP β-subunit (CD0725) and methyltetrahydrofolate methyltransferase (CD0727) were cloned into the pSOS94 vector, under the control of phosphate butyryltransferase (ptb) promoter. Genes CD0725, CD0726 and CD0727 were PCR amplified from *C. difficile* genomic DNA (ATCC: BAA-1382™) using cd0725_fwd and cd0727_rev primers, excluding the natural promoter. This 3.1 kb PCR product was re-amplified using Fwd_0725_BamHI and Rev_0727_KasI primers, to include BamHI and KasI restriction sites on either ends of the PCR product. The PCR product, digested with BamHI and KasI, was ligated to the linearized pSOS94 vector having suitable sticky ends to generate p94CD0725-27 plasmid (FIG. 8). All primers used for plasmid construction are listed in Table 2.

TABLE 2

Primers used for the construction of p94CD0725-27 and RT-PCR confirmation

| Primer Name | Sequence (5'→3') |
|---|---|
| CD0725_fwd | AGAATTAAAATAGGCTTAAGGGGG (SEQ ID NO: 2) |
| CD0727_rev | CTATTTCCCCCTTTAATATTTACACC (SEQ ID NO: 3) |
| Fwd_0725_BamHI | AAGGATCCAGGAGGATGGCATTTAAAATGTCTACTCAAAATA (SEQ ID NO: 4) |
| Rev_0727_KasI | AAGGCGCCCTAGAAAGCAAATCCACCTTCA (SEQ ID NO: 5) |
| RT_fwd_cd0725 | GCTAATTGTCCAGTAGAGTGGGCT (SEQ ID NO: 6) |
| RT_rev_cd0725 | ACTGCCTTAGCTACATCAGCAC (SEQ ID NO: 7) |
| RT_fwd_cd0726 | TGCCCACATATGTCTGATGACGCT (SEQ ID NO: 8) |
| RT_rev_cd0726 | TACTCAGATGCACCAGCACCAACT (SEQ ID NO: 9) |

TABLE 2-continued

Primers used for the construction of p94CD0725-27 and RT-PCR confirmation

| Primer Name | Sequence (5'→3') |
|---|---|
| RT_fwd_cd0727 | ACTCTGCTGATGCTGGCTCAAGAT (SEQ ID NO: 10) |
| RT_rev_cd0727 | TGGCAGTAAGCCATACGCTCATCA (SEQ ID NO: 11) |

The p94CD0725-27 plasmid was transformed into TOP10 chemically competent E. coli cells (Invitrogen) according to user guidelines. Sequence and orientation of the insert in the plasmid was confirmed using sequencing reaction. To avoid natural restriction system of C. acetobutylicum, p94CD0725-27 was methylated by transforming it into E. coli ER2275 containing pANI plasmid. Methylated plasmid was then transformed into C. acetobutylicum by electroporation to generate C. acetobutylicum 824(p94CD0725-27) strain (abbreviated as 824(p94CD0725-27)).

EXAMPLE 2

Expression of mRNA in the 824(p94CD0725-27) Strain

Figure 9:
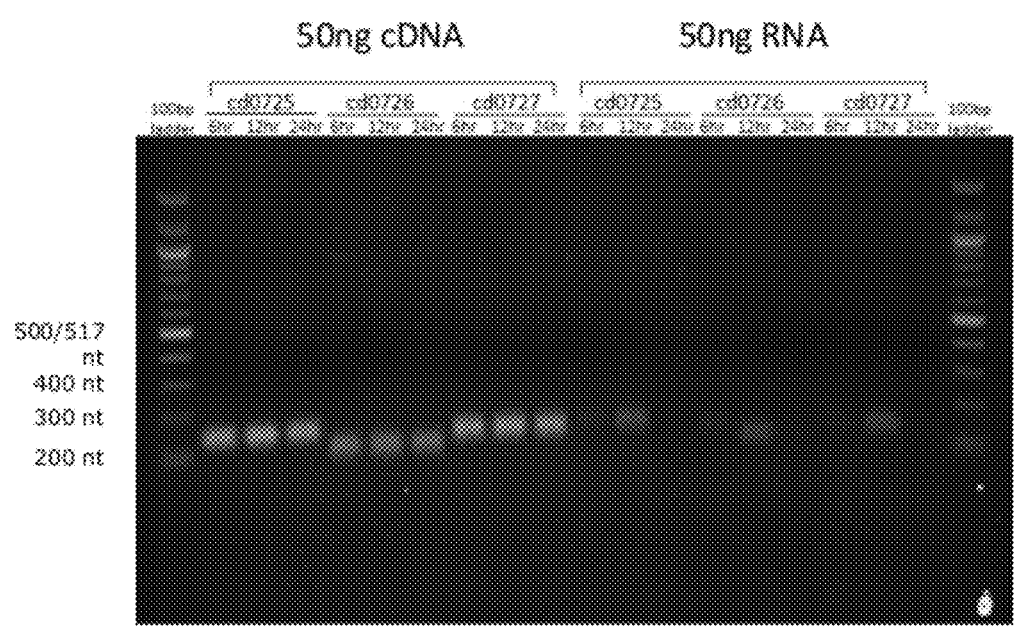
FIG. 9 shows the expression of CD0725, CD0726 and CD0725 in *C. acetobutylicum* by semi-quantitative RT-PCR on the p94CD0725-27 strain.

The expression of mRNA from p94CD0725-27 plasmid was determined. Semi-quantitative RT-PCR was performed on mid-exponential (6 hr), early stationary (12 hr) and stationary (24 hr) phase cultures of the 824(p94CD0725-27) strain (FIG. 9). Reverse transcription of total RNA was carried out with random hexamer primers using High Capacity cDNA ReverseTranscription Kit (Applied Biosystems). PCR was performed on 50 ng of cDNA using primers specific to CD0725, CD0726 and CD0727 (Table 2). To test for DNA contamination during RNA isolation, equal amount of RNA was used as a template for PCR using the primer sets as mentioned above. With minimal or no DNA contamination in RNA isolates, the expression of mRNA from p94CD0725-27 plasmid was confirmed (FIG. 9).

EXAMPLE 3

Cell Growth in the 824(p94CD0725-27) Strain

Figure 10:
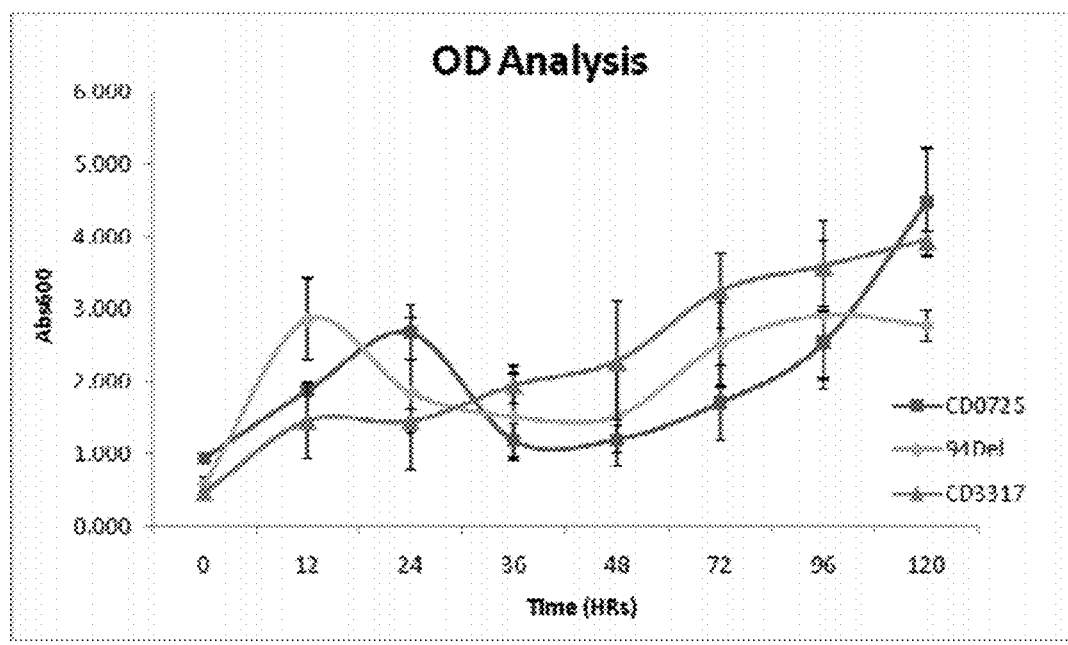
FIG. 10 shows cell growth ($Abs_{600}$) profile of the 824 (p94CD0725-27) strain and the 824(pSOS94del) plasmid control strains of *C. acetobutylicum*.
Figure 11:
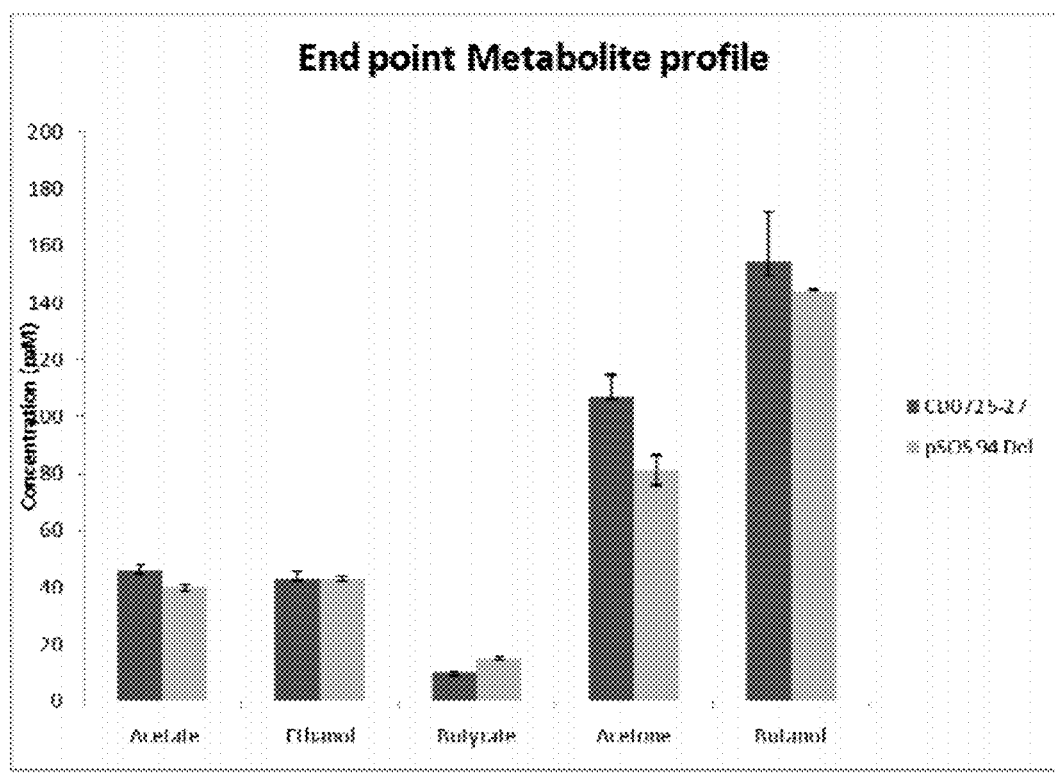
FIG. 11 shows an end point (120 hr) HPLC analysis for supernatant sample of the 824(p94CD0725-27) strain and the 824(pSOS94del) plasmid control strains of *C. acetobutylicum*.

The 824(p94CD0725-27) strain reached similar cell densities to that of its plasmid control (FIG. 10). Although the 824(p94CD0725-27) strain had similar growth profile in exponential phase and stationary phase, it attained a higher OD ($A_{600}$) than its plasmid control towards the end of 5 day static flask fermentation (FIG. 10). End point HPLC analysis (120 hr) on supernatant samples of the 824(p94CD0725-27) strain showed it produced somewhat higher levels of solvents apparently due to the expression of these transgenes (FIG. 11).

EXAMPLE 4

Ability of the Cac(p1/3) Strain to Use $CO_2$ in the Presence of $H_2$

Test experiments were carried out for $^{14}C$ distributions from $^{14}C$-bicarbonate for both C. ljungdahlii (CLJ) and C. acetobutylicum (CAC; WT and strain Cac(p1/3). Cac(p1/3) expressed 3 WL pathway genes, and was the same as the 824(p94CD0725-27) strain described in Examples 1-3.

For primary cultures C. acetobutylicum and C. ljungdahlii were grown on CGM and ATCC 1754, respectively, using fructose as a carbon source. A 10% inoculum from exponentially growing primary culture was transferred to 150 ml anaerobic serum bottles, containing 30 ml of sugar-free media containing 1-2 µCi of sodium [14C] carbonate, for growth on $CO_2$ as sole source of carbon. Cultures were grown at 37° C. at 110 rpm for 48 hrs before harvesting. $CO_2$ from the head space, biomass and cell supernatant were collected and analyzed by the scintillating counter $^{14}C$ in the biomass represents $CO_2$ incorporation, $^{14}C$ counts in the supernatant include bicarbonate, dissolved $CO_2$ and metabolites, and gaseous $^{14}C$ counts represents the non-assimilated $CO_2$, which is converted from bicarbonate.

Figure 12:
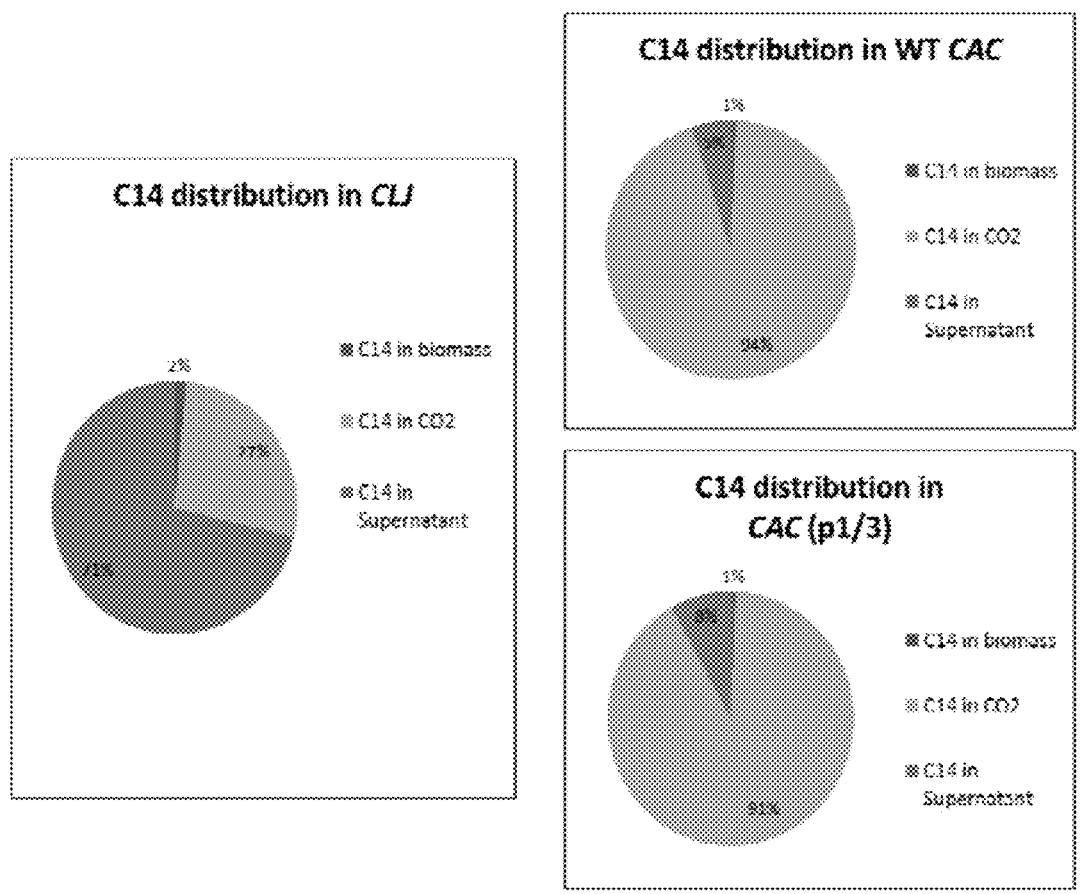
FIG. 12 shows incorporation of $^{14}C$ in *C. acetobutylicum* (WT and the recombinant strain Cac(p1/3) and the WT *C. ljungdahlii*.

Fractions of $^{14}C$ distributed into biomass, gaseous $CO_2$ and in soluble extracellular products in the medium, plus the errors associated with such measurements are shown in FIG. 12. More $CO_2$ ($^{14}C$ labeled) was incorporated and released mainly as end products into the medium, by C. ljungdahlii than by C. acetobutylicum (WT CAC and Cac (p1/3) strain). A small amount of $^{14}C$ was incorporated into the biomass in C. acetobutylicum, which is not an artifact of an experimental error since it was also recently shown by others that WT C. acetobutylicum fixes some $CO_2$. $^{14}C$ from bicarbonate was either going into biomass or products produced by the cells (acetate and/or ethanol for C. ljungdahlii or acetate, butyrate, acetone, butanol and ethanol for C. acetobutylicum) or converted to gaseous $CO_2$. As shown in FIG. 12, relatively little $^{14}C$ went into biomass even for C. ljungdahlii, which grew well on $CO_2/H_2$. Most $^{14}C$ went into extracellular products (and thus into the supernatant of the culture). The recombinant C. acetobutylicum strain Cac(p 1/3) incorporated more into extracellular products than the WT CAC, thus demonstrating that the cloned heterologous WL genes are functional in C. acetobutylicum and altering cell metabolism.

EXAMPLE 5

Construction of pJIR750_CD3317728

Two genes, formate dehydrogenase (CD3317) and acetyl-CoA synthase (CD0728), were cloned into the pJIR750 vector to make a synthetic operon under the expression of thiolase (thl) promoter. The two genes CD3317 and CD0728 were PCR amplified from C. difficile genomic DNA using CD3317_fwd/rev and CD0728_fwd/rev primers, respectively (Table 3).

TABLE 3

Primers used for the construction of pJIR750_CD3317728

| Primer Name | Sequence (5'→3') |
|---|---|
| CD3317_fwd | GGGAATTGTATGGAGAAAAAATTTTA (SEQ ID NO: 12) |
| CD3317_rev | GCCTTTCTGCCTTTTATAAATCTTAAATC (SEQ ID NO: 13) |
| CD0728_fwd | GGGAAATAGAATGAATCTATATAATATAA (SEQ ID NO: 14) |
| CD0728_rev | AAATTTTCCATCAATTACATTACAC (SEQ ID NO: 15) |
| CD0728_KasI_fwd | AAGGCGCCGAATGAATCTATATAATATAATCTTTA (SEQ ID NO: 16) |
| CD0728_KasI_rev | AAGGCGCCTTACATTACACTTTCCATAGC (SEQ ID NO: 17) |
| CD3317_BamHI_fwd | AAGGATCCAGGAGGATGGAGAAAAAATTTTTACAGTTTG (SEQ ID NO: 18) |
| CD3317_KasI_rev | AAGGCGCCTTAGATATTTGTAGCTGTCATTTT (SEQ ID NO: 19) |

Figure 13:
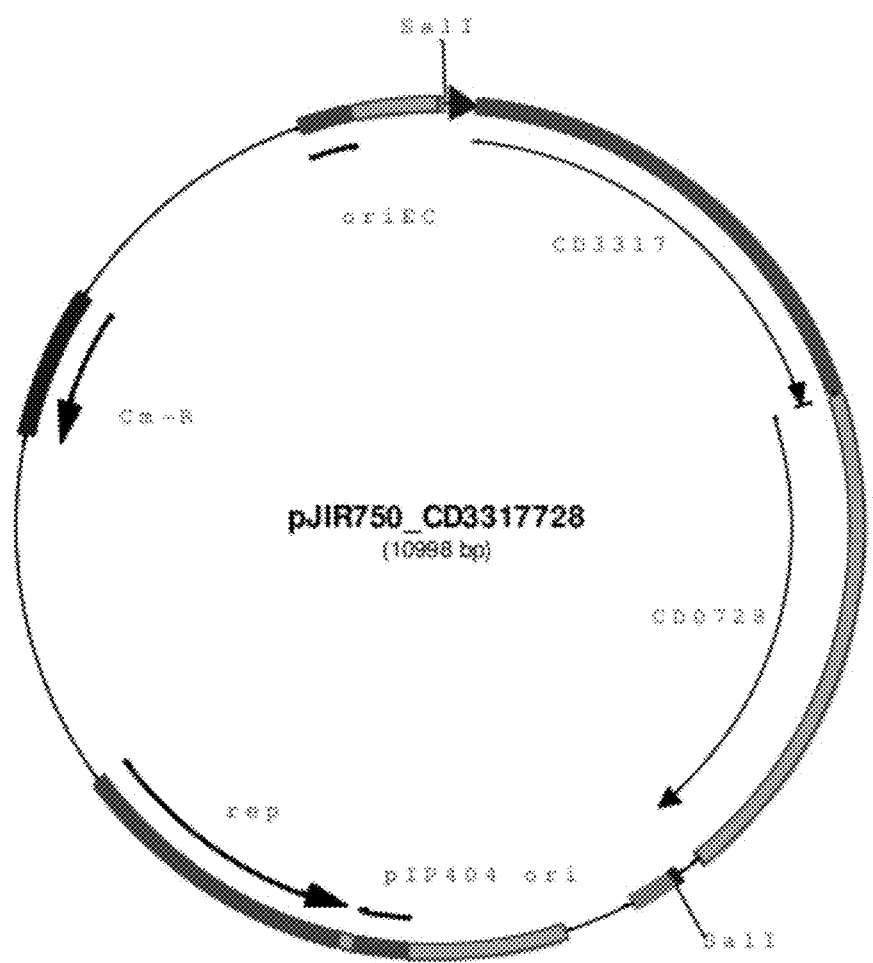
FIG. 13 shows the map of pJIR750_CD3317728. Cm-R region codes for chloramphenicol/thiamphenicol resistance.

CD3317 and CD0728 were re-amplified to include BamHI and KasI restriction sites to 5' and 3' ends of the PCR product, respectively (Table 3). The CD3317 gene, digested with BamHI and KasI was ligated into linearized pSOS95del vector under thl promoter, to generate p95CD3317 plasmid. The CD0728 gene, digested with KasI, was ligated to linearized p95CD3317 vector with compatible sticky ends to generate p95CD3317-728. The synthetic operon along with thl promoter was fragmented out of the p95CD3317-728 by digesting the plasmid with SalI. This vector fragment was ligated into linearized destination vector, pJIR750, with compatible sticky, to generate pJIR750_CD3317728 (FIG. 13).

p95CD3317 plasmid that is described above was methylated and transformed into *C. acetobutylicum* by the methods mentioned above for p94CD0725-27, to generate *C. acetobutylicum* 824(p95CD3317) strain.

Figure 14:
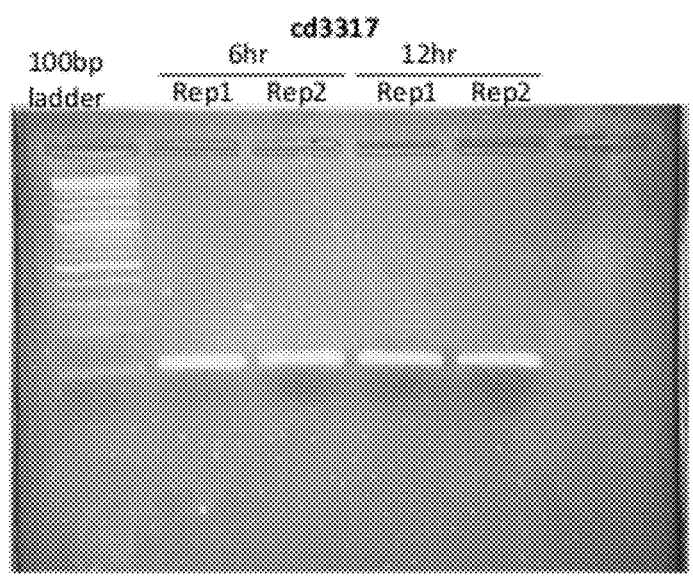
FIG. 14 shows the mRNA expression of CD3317 in *C. acetobutylicum* by semi-quantitative RT-PCR on the 824 (p95CD3317) strain.

Expression of mRNA from p95CD3317 plasmid was determined by performing a semi-quantitative RT-PCR on mid-exponential (6 hr) and early stationary (12 hr) phase cultures of the 824(p95CD3317) strain (FIG. 14) using methodology described in Example 2. To test for DNA contamination during RNA isolation, equal amount of RNA was used as template for PCR as described above for p94CD0725-27. In a cell growth test as described in Example 3, the 824 (p95CD3317) strain reached similar optical densities to that of 824(p94CD0725-27) strain (FIG. 10).

---

What is claimed:

1. A recombinant *Clostridium* expressing one or more heterologous Wood-Ljungdahl (WL) genes derived from a donor *Clostridium*, wherein the recombinant *Clostridium* is derived from a recipient *Clostridium*, wherein the recipient *Clostridium* does not have a functional WL pathway, wherein the donor *Clostridium* has a functional WL pathway, and wherein the recombinant *Clostridium* has a functional WL pathway.

2. The recombinant *Clostridium* of claim 1, wherein the recombinant *Clostridium* produces a metabolite at an increased level compared with the recipient *Clostridium*.

3. The recombinant *Clostridium* of claim 2, wherein the metabolite is a chemical, biofuel, or biofuel precursor.

4. The recombinant *Clostridium* of claim 3, wherein the chemical is selected from the group consisting of a carboxylic acid, isopropanol, butanediol, acetoin and propanediol.

5. The recombinant *Clostridium* of claim 4, wherein the carboxylic acid is butyrate or acetate.

6. The recombinant *Clostridium* of claim 3, wherein the biofuel is selected from the group consisting of ethanol, n-butanol, i-butanol and 2-butanol.

7. The recombinant *Clostridium* of claim 1, wherein the recipient *Clostridium* is employed to produce a metabolite.

8. The recombinant *Clostridium* of claim 1, wherein the recipient *Clostridium* is a solventogenic *Clostridium*.

9. The recombinant *Clostridium* of claim 8, wherein the solventogenic *Clostridium* is selected from the group consisting of *C. acetobutylicum*, *C. beijerinckii*, *C. saccharoperbutylacetonicum*, and *C. madisonii*.

10. The recombinant *Clostridium* of claim 1, wherein the recipient *Clostridium* is *C. acetobutylicum*.

11. The recombinant *Clostridium* of claim 1, wherein the recipient *Clostridium* is a cellulolytic *Clostridium*.

12. The recombinant *Clostridium* of claim 11, wherein the cellulolytic *Clostridium* is selected from the group consisting of *C. thermocellum*, *C. phytofermentans*, and *C. cellulolyticum*.

13. The recombinant *Clostridium* of claim 1, wherein the donor *Clostridium* is selected from the group consisting of *M. thermoacetica*, *C. carboxidivorans*, *C. difficile*, and *C. ljungdahlii*.

14. The recombinant *Clostridium* of claim 1, wherein the donor *Clostridium* is *C. difficile* or *C. ljungdahlii*.

15. The recombinant *Clostridium* of claim 1, wherein at least one of the one or more heterologous Wood-Ljungdahl pathway genes is integrated into the genome of the recombinant *Clostridium*.

16. A method of producing a metabolite, comprising
   (a) culturing the recombinant *Clostridium* of claim 1 in a culture medium, whereby the recombinant *Clostridium* produces the metabolite at an increased level compared with the recipient *Clostridium*, and
   (b) recovering the metabolite from the recombinant *Clostridium* or the culture medium.

17. The method of claim 16, wherein the metabolite is selected from the group consisting of acetate, ethanol, butyrate, acetoin and butanol.

18. The method of claim 16, wherein the recipient *Clostridium* is *C. acetobutylicum*.

19. The method of claim 16, wherein the donor *Clostridium* is *C. difficile* or *C. ljungdahlii*.

* * * * *

SEQUENCE LISTING

<160> NUMBER OF SEQ ID NOS: 19

<210> SEQ ID NO 1
<211> LENGTH: 336
<212> TYPE: DNA
<213> ORGANISM: Artificial Sequence
<220> FEATURE:
<223> OTHER INFORMATION: synthetic

<400> SEQUENCE: 1

```
atggtaagca ggtacgtacc tgatatggga gatttaatat gggttgattt tgatcctaca      60
aaaggaagtg agcaagctgg acatagacca gctgttgttt taagtccttt tatgtataat     120
aataaaacag gaatgtgttt atgtgttcct tgtacaacac aatcaaaagg atatccttt      180 gaagttgttt tatcaggaca agaaagagat ggagtagcat tagctgatca agtaaaaagt     240
atagcatgga gagcaagagg agcaacaaaa aaaggaacag ttgcaccaga ggaattacaa     300
ttaataaaag caaaaataaa tgtattaata ggatag                               336
```

<210> SEQ ID NO 2
<211> LENGTH: 24
<212> TYPE: DNA
<213> ORGANISM: Artificial Sequence
<220> FEATURE:
<223> OTHER INFORMATION: primer

<400> SEQUENCE: 2

```
agaattaaaa taggcttaag gggg                                             24
```

<210> SEQ ID NO 3
<211> LENGTH: 26
<212> TYPE: DNA
<213> ORGANISM: Artificial Sequence
<220> FEATURE:
<223> OTHER INFORMATION: primer -continued

<400> SEQUENCE: 3
ctatttcccc ctttaatatt tacacc                                          26

<210> SEQ ID NO 4
<211> LENGTH: 43
<212> TYPE: DNA
<213> ORGANISM: Artificial Sequence
<220> FEATURE:
<223> OTHER INFORMATION: primer

<400> SEQUENCE: 4
aaggatccag gaggatggca tttaaaatgt ctactcaaaa ata                       43

<210> SEQ ID NO 5
<211> LENGTH: 30
<212> TYPE: DNA
<213> ORGANISM: Artificial Sequence
<220> FEATURE:
<223> OTHER INFORMATION: primer

<400> SEQUENCE: 5
aaggcgccct agaaagcaaa tccaccttca                                      30

<210> SEQ ID NO 6
<211> LENGTH: 24
<212> TYPE: DNA
<213> ORGANISM: Artificial Sequence
<220> FEATURE:
<223> OTHER INFORMATION: primer

<400> SEQUENCE: 6
gctaattgtc cagtagagtg ggct                                            24

<210> SEQ ID NO 7
<211> LENGTH: 22
<212> TYPE: DNA
<213> ORGANISM: Artificial Sequence
<220> FEATURE:
<223> OTHER INFORMATION: primer

<400> SEQUENCE: 7
actgccttag ctacatcagc ac                                              22

<210> SEQ ID NO 8
<211> LENGTH: 24
<212> TYPE: DNA
<213> ORGANISM: Artificial Sequence
<220> FEATURE:
<223> OTHER INFORMATION: primer

<400> SEQUENCE: 8
tgcccacata tgtctgatga cgct                                            24

<210> SEQ ID NO 9
<211> LENGTH: 24
<212> TYPE: DNA
<213> ORGANISM: Artificial Sequence
<220> FEATURE:
<223> OTHER INFORMATION: primer

<400> SEQUENCE: 9
tactcagatg caccagcacc aact                                            24

<210> SEQ ID NO 10
<211> LENGTH: 24

```
<212> TYPE: DNA
<213> ORGANISM: Artificial Sequence
<220> FEATURE:
<223> OTHER INFORMATION: primer

<400> SEQUENCE: 10
actctgctga tgctggctca agat                                    24

<210> SEQ ID NO 11
<211> LENGTH: 24
<212> TYPE: DNA
<213> ORGANISM: Artificial Sequence
<220> FEATURE:
<223> OTHER INFORMATION: primer

<400> SEQUENCE: 11
tggcagtaag ccatacgctc atca                                    24

<210> SEQ ID NO 12
<211> LENGTH: 27
<212> TYPE: DNA
<213> ORGANISM: Artificial Sequence
<220> FEATURE:
<223> OTHER INFORMATION: primer

<400> SEQUENCE: 12
gggaattgta tggagaaaaa aattta                                  27

<210> SEQ ID NO 13
<211> LENGTH: 29
<212> TYPE: DNA
<213> ORGANISM: Artificial Sequence
<220> FEATURE:
<223> OTHER INFORMATION: primer

<400> SEQUENCE: 13
gcctttctgc cttttataaa tcttaaatc                               29

<210> SEQ ID NO 14
<211> LENGTH: 29
<212> TYPE: DNA
<213> ORGANISM: Artificial Sequence
<220> FEATURE:
<223> OTHER INFORMATION: primer

<400> SEQUENCE: 14
gggaaataga atgaatctat ataatataa                               29

<210> SEQ ID NO 15
<211> LENGTH: 25
<212> TYPE: DNA
<213> ORGANISM: Artificial Sequence
<220> FEATURE:
<223> OTHER INFORMATION: primer

<400> SEQUENCE: 15
aaatttccca tcaattacat tacac                                   25

<210> SEQ ID NO 16
<211> LENGTH: 35
<212> TYPE: DNA
<213> ORGANISM: Artificial Sequence
<220> FEATURE:
<223> OTHER INFORMATION: primer

<400> SEQUENCE: 16
```

```
aaggcgccga atgaatctat ataatataat cttta                                      35

<210> SEQ ID NO 17
<211> LENGTH: 29
<212> TYPE: DNA
<213> ORGANISM: Artificial Sequence
<220> FEATURE:
<223> OTHER INFORMATION: primer

<400> SEQUENCE: 17
aaggcgcctt acattacact ttccatagc                                             29

<210> SEQ ID NO 18
<211> LENGTH: 40
<212> TYPE: DNA
<213> ORGANISM: Artificial Sequence
<220> FEATURE:
<223> OTHER INFORMATION: primer

<400> SEQUENCE: 18
aaggatccag gaggatggag aaaaaaattt ttacagtttg                                 40

<210> SEQ ID NO 19
<211> LENGTH: 32
<212> TYPE: DNA
<213> ORGANISM: Artificial Sequence
<220> FEATURE:
<223> OTHER INFORMATION: primer

<400> SEQUENCE: 19
aaggcgcctt agatatttgt agctgtcatt tt                                         32
```